(12) United States Patent
Devisetty et al.

(10) Patent No.: US 6,984,609 B2
(45) Date of Patent: Jan. 10, 2006

(54) CONCENTRATED, WATER-SOLUBLE, GRANULAR PLANT GROWTH REGULATOR FORMULATION AND METHODS FOR USE OF SAME

(75) Inventors: Bala N. Devisetty, Buffalo Grove, IL (US); Robert M. Beach, Grayslake, IL (US); Ricardo A. Menendez, Vernon Hills, IL (US); Prem Warrior, Green Oaks, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 0 days.

(21) Appl. No.: 10/120,862

(22) Filed: Apr. 11, 2002

(65) Prior Publication Data

US 2003/0008949 A1    Jan. 9, 2003

Related U.S. Application Data

(60) Provisional application No. 60/283,217, filed on Apr. 11, 2001.

(51) Int. Cl.
*A01N 43/02*    (2006.01)

(52) U.S. Cl. ............ 504/116.1; 504/140; 524/17; 524/20; 524/47; 524/48; 524/56; 524/58; 524/72; 524/73; 524/376; 524/387

(58) Field of Classification Search ............ 504/116.1, 504/140; 524/17, 20, 47, 48, 56, 58, 72, 524/73, 376, 387
See application file for complete search history.

(56) References Cited

U.S. PATENT DOCUMENTS

| | | | | |
|---|---|---|---|---|
| 3,025,168 A | * | 3/1962 | Greenberg | 426/55 |
| 3,062,636 A | * | 11/1962 | Regenstein, Jr. | 504/140 |
| 3,083,089 A | * | 3/1963 | Renner | 504/126 |
| 3,737,298 A | * | 6/1973 | Fielding | 504/348 |
| 3,738,822 A | * | 6/1973 | Asahi et al. | 504/297 |
| 4,104,052 A | * | 8/1978 | Szkrybalo | 504/293 |
| 4,359,576 A | * | 11/1982 | Ten Haken et al. | 544/336 |
| 4,361,436 A | * | 11/1982 | McCarthy et al. | 504/128 |
| 4,563,212 A | | 1/1986 | Becher et al. | |
| 4,762,549 A | * | 8/1988 | Rajadhyaksha | 504/358 |
| 4,936,901 A | | 6/1990 | Surgant, Sr. et al. | |
| 5,198,254 A | * | 3/1993 | Nisperos-Carriedo et al. | 426/102 |
| 5,292,533 A | | 3/1994 | McMahon et al. | |
| 5,376,391 A | * | 12/1994 | Nisperos-Carriedo et al. | 426/102 |
| 5,441,923 A | * | 8/1995 | Tocker | 504/125 |
| 5,474,971 A | | 12/1995 | Sandell | |
| 5,622,658 A | | 4/1997 | Lloyd et al. | |
| 5,693,592 A | | 12/1997 | Illingworth | |
| 5,750,472 A | * | 5/1998 | Yvin et al. | 504/292 |
| 6,087,306 A | * | 7/2000 | Bell et al. | 504/367 |
| 6,114,284 A | * | 9/2000 | Fujisawa et al. | 504/140 |
| 6,306,417 B2 | * | 10/2001 | Koike | 424/417 |
| 6,387,388 B1 | * | 5/2002 | Misselbrook et al. | 424/409 |

FOREIGN PATENT DOCUMENTS

| | | |
|---|---|---|
| EP | 0252897 | 1/1988 |
| WO | WO 93/25074 | 12/1993 |
| WO | WO 97/16968 | 5/1997 |

* cited by examiner

*Primary Examiner*—Bernard Lipman
(74) *Attorney, Agent, or Firm*—Wood, Phillips, Katz, Clark & Mortimer

(57) ABSTRACT

A water-soluble granular composition including at least 40% of at least one plant growth regulator, at least one binder, at least one disaccharide and at least one surfactant; as well as methods for making and using the composition are disclosed. The water-soluble granular composition advantageously improves preparation of a solid plant growth regulator formulation for spray application, as such composition swiftly dissolves, is easily metered for application, can be more highly concentrated and is dust-free. A presently preferred water-soluble granular composition includes at least 40% of at least one gibberellin as the plant growth regulator.

13 Claims, No Drawings

CONCENTRATED, WATER-SOLUBLE, GRANULAR PLANT GROWTH REGULATOR FORMULATION AND METHODS FOR USE OF SAME

CROSS REFERENCE TO RELATED APPLICATIONS

This application is based upon and claims the priority of provisional application Ser. No. 60/283,217, filed Apr. 11, 2001.

FIELD OF THE INVENTION

The present invention is directed to a water-soluble granular composition including at least 40% of at least one plant growth regulator, at least one binder, at least one disaccharide and at least one surfactant; as well as methods for making and using the composition. The water-soluble granular composition advantageously improves preparation of a solid plant growth regulator formulation for spray application, as such composition swiftly dissolves, is easily metered, can be more highly concentrated and is dust-free. A presently preferred water-soluble granular composition includes at least 40% of at least one gibberellin as the plant growth regulator.

BACKGROUND OF THE INVENTION

Plant growth regulators are useful for influencing a range of plant developmental processes including stem elongation, germination, dormancy, flowering, sex expression, enzyme induction, fruit size and quality, as well as leaf and fruit senescence. Plant growth regulators may be formulated in at least five different types of formulations: 1) solutions, 2) wettable powders, 3) soluble powders, 4) tablets and 5) water-dispersible granules. In order to use such formulations, they must be diluted in aqueous solution prior to conventional spray application. Each of the conventional types of formulations has disadvantages, so research to provide improved plant growth regulator formulations continues. The disadvantages of the conventional formulations will be discussed with reference to a specific plant growth regulator class, the gibberellins, as representative of conventional formulations of plant growth regulators in general.

Gibberellins are one class of plant growth regulators which are diterpenoid acids. Gibberellins are commercially produced by fermentation of a natural fungus, *Gibberella fugikuroi*. Gibberellins are marketed under various trade names and are commercially used on a variety of fruit orchards, vegetable crops, row crops, and ornamental crops. The predominantly used gibberellic acid is $GA_3$, formulated in any of the five forms described above. The other commonly used gibberellins are a combination of two, $(GA_{4+7})$ which are primarily formulated as solutions either in tetrahydrofurfurryl alcohol (THFA) or in propylene glycol.

Solution Formulations

Gibberellin solution formulations are disadvantageous in several respects. The solutions, such as those of $GA_{4+7}$ in propylene glycol, are less concentrated due to low solubility of actives, and have limited stability. Of the currently used solvents, isopropyl alcohol and methyl alcohol offer severe disadvantages such as flammability and toxicity, which lead to restrictions in manufacturing, packaging, labeling, transportation, and warehousing of such solutions. THFA, used in some of the formulations, is considered corrosive to the eye and skin. Moreover, low solubility of gibberellins in propylene glycol does not permit preparation of high potency solution formulations. These low strength solution formulations also require larger packaging, more storage space, and higher associated transportation, warehousing, and container disposal costs. Due to very low solubility and undesirable hydrolysis, it has not been possible to formulate gibberellins in aqueous systems. Some examples of solution formulations of gibberellins include PROGIBB 4%, RALEX, RELEASE LC and RYZUP, all available from Valent BioSciences Corp.

Powder Formulations

A soluble powder formulation is one which, when mixed with water, dissolves readily in water and forms a true solution. Once the solution is formed, no further mixing or agitation of the tank-mix is required.

Mixing is a process of combining different materials, usually to a homogeneous state. Agitation aids the process of mixing, and is a mechanical process involving rotating shafts of blades in the bottom of the spray tank.

An example of a powder gibberellin formulation is PROGIBB 2X, available from Valent BioSciences Corp., which contains 20% of the active ingredient, gibberellin. A wettable powder formulation is a dry, finely ground formulation. In this formulation, the active ingredient is combined with a finely ground dry carrier, usually a mineral clay, along with other ingredients that enhance the ability of the powder to be suspended in water. Upon mixing the wettable powder with water, a suspension is formed, which is then applied by a spray technique. Examples of a wettable powder gibberellin formulation include PROGIBB PLUS, ACTIVOL 10% and RELEASE, all available from Valent BioSciences Corp.

The primary disadvantage of wettable powder and soluble powder formulations is that they tend to produce dust upon handling, such as when pouring, transferring or measuring them. This dust may pose health hazards. Further, powder formulations tend to wet poorly and also solubilize slowly upon addition to water. Powder formulations thus take longer times to wet, disperse and solubilize in the tank-mix. Formation of lumps or partially solubilized spray solutions will lead to uneven distribution of the plant growth regulator in the tank-mix with potential for reduced field performance. Sometimes, foam in the spray tank caused by spray tank adjuvants can also affect wetting and solubility of wettable and soluble powders. Wettable powder formulations will also leave undesirable insoluble residues both in the tank and on the sprayed foliage and fruit.

Tablet Formulations

Tablet formulations are pre-measured dosage delivery systems. They are useful in small areas, or for ornamental purposes. Tablet formulations may be effervescent, which dissolve in water over a period of two to ten minutes depending upon the type and size of the tablet.

However, tablets deliver only between 0.1–1 gram of active ingredient per tablet. They are not ideal for large-scale field operations. Moreover, effervescent tablets are highly susceptible to humidity; may be slow to dissolve and are expensive.

Water-Dispersible Granular Formulations

Water-dispersible granules are also known as wettable granules or dry flowables. This type of formulation is similar to a wettable powder, except that the active ingredient is formulated as a dispersible granule. To prepare the water-dispersible granules for spray application, they are dispersed in water and form a suspension upon agitation. Many different water-dispersible granular formulations are known for agricultural chemicals. For example, EP 0 252 897 and U.S. Pat. No. 4,936,901 disclose encapsulated plant growth regulators in water dispersible granular formulations; and U.S. Pat. No. 5,622,658 discloses an extrudable composition for preparing water-dispersible granules. An example of a granular gibberellin formulation containing 3.1% active ingredient is Gibberellin Kyowa Soluble Powder, available from Kyowa Fermentation Industry of Japan.

Water-dispersible granules usually have no greater than eight percent moisture content, and form suspensions when added to aqueous solutions. The resulting suspension must be agitated for a period of time in order to fully disperse it. Agitation or by-pass recirculation of the tank-mix must also be maintained during application. The quality of water-dispersible granules is highly process- and active-ingredient-dependent; and can result in low yield recoveries, poor attrition resistance leading to dust potential, high manufacturing cost and poor dispersion. Generally, sprays of dissolved water-dispersible granular formulations leave undesirable insoluble residues on the treated foliage and fruit.

For plant growth regulators such as gibberellins to be efficacious, the active ingredient must solubilize in the tank-mixes prior to application. Otherwise, product efficacy will be severely affected. When water-dispersible granules are used, the grower often may not be able to realize if he had achieved the total solubility of the active ingredient in the spray solutions. In addition, water-dispersible granules can become hardened over time and thus result in poor dispersibility and solubility of the active ingredient. Dust and caking may be problems with certain water-dispersible granules and powder formulations.

Therefore, a plant growth regulator formulation which provides high potency and rapid solubility; and avoids the problems associated with conventional formulations, would be advantageous.

BRIEF SUMMARY OF THE INVENTION

The present invention is directed to a water-soluble granular composition including at least 40% of at least one plant growth regulator, at least one binder, at least one disaccharide and at least one surfactant; as well as methods for making and using the composition. The water-soluble granular composition advantageously improves preparation of a solid plant growth regulator formulation for spray application, as such composition swiftly dissolves, is easily metered, can be more highly concentrated and is dust-free for handling. A presently preferred water-soluble granular composition includes at least one gibberellin, polyvinylpyrrolidone, at least one disaccharide and at least one surfactant.

The invention is directed to a water-soluble granular composition comprising: at least one plant growth regulator; at least one binder; at least one disaccharide; and at least one surfactant. More specifically, the plant growth regulator may be a gibberellin, an auxin, an organic acid, a cytokinin, an ethylene biosynthesis inhibitor or a combination thereof; the binder may be polyvinylpyrrolidone, a lignosulfonate, a lignin, a lecithin, a starch, a gluten, a polyethylene glycol or a combinations thereof; the disaccharide may be sucrose, lactose, maltose, hydrolyzed starches such as maltodextrin and corn syrup solids, sugar alcohols such as sorbitol and mannitol and other sugars such as glucose and fructose or a combination thereof; the surfactant may be an ethoxylated fatty acid, a glycol ester, an ethoxylated alcohol, a sorbitan fatty acid ester or a combination thereof. The composition may also contain at least one additional component such as a surface active agent, a sticker, a spreader sticker, a nematicide, a systemic acquired resistance inducer, an anti-foaming agent, a preservative, a humectant, a dye, a U.V. protectant, a buffer, a flow agent, a carrier or a combination thereof.

The composition may have from about 40 to about 80 weight percent plant growth regulator, from about 0.1 to about 10 weight percent binder, from about 5 to about 95 weight percent disaccharide and from about 0.1 to about 10 weight percent surfactant.

A preferred formulation is a water-soluble granular gibberellin composition comprising: at least 40% of at least one gibberellin, at least one binder, at least one disaccharide and at least one surfactant. A presently preferred disaccharide is lactose monohydrate, a presently preferred binder is polyvinylpyrrolidone and a presently preferred surfactant is a polyoxyethylene 20 monolaurate. The composition may also include an additional plant growth regulator such as a different gibberellin, an auxin, a cytokinin, an organic acid, an ethylene biosynthesis inhibitor or a combination thereof. The composition may have from about 40 to about 50 weight percent gibberellin, from about 0.1 to about 4 weight percent polyvinylpyrrolidone, from about 40 to about 60 weight percent lactose monohydrate and from about 0.5 to about 5 weight percent polyoxyethylene 20 monolaurate.

The invention is also directed to a method of regulating plant growth comprising the step of treating soil, a seed or a plant with an effective growth-regulating amount of the composition described above. The composition may be diluted with water and spray-applied. For example, when the plant is a fruit-producing plant, such as a grape plant, a grape-producing plant so treated produces larger grapes and/or grapes having higher percentage of soluble solids.

The invention is also directed to a method of preparing a water-soluble, granular plant growth regulator formulation comprising the steps of:

- sizing particles of a plant growth regulator and a disaccharide separately to produce a fine powder of plant growth regulator and a fine powder of disaccharide;
- blending said fine powder of plant growth regulator and said fine powder of disaccharide to produce a homogeneous mixture;
- preparing an aqueous solution of polyvinylpyrrolidone and a surfactant;
- combining said aqueous solution and said homogeneous mixture to form an extrudable blend;
- extruding said extrudable blend to form an extruded material;
- drying said extruded material; and then,
- sieving and recovering water-soluble granules of a plant growth regulator formulation.

In this method, the plant growth regulator may be gibberellin and the disaccharide may be lactose monohydrate.

The invention is also directed to a method of enhancing the utilization of a solid plant growth regulator formulation for spray application comprising the step of formulating said plant growth regulator in a water-soluble granular formulation containing at least 40% of plant growth regulator. In the method, preparation of the formulation for spray application can be enhanced, since dust from the solid formulation can be eliminated upon transfer; accurate metering and rapid dissolution of the solid formulation can be attained. The method is also advantageous because the solid formulation contains twice the concentration of plant growth regulators as conventional formulations of plant growth regulators. A presently preferred formulation for use in the method is a water-soluble granular formulation which contains at least one plant growth regulator, at least one binder, at least one disaccharide and at least one surfactant. A presently most preferred formulation is a water-soluble granular formulation which contains at least one gibberellin, polyvinylpyrrolidone, lactose monohydrate and polyoxyethylene 20 monolaurate.

DETAILED DESCRIPTION OF THE INVENTION

We have now surprisingly discovered that solid formulations of plant growth regulators are improved if in the form of water-soluble granules. The water-soluble granular formulation readily dissolves in water to form a true solution, so that extended mixing or occasional or continuous agitation of the spray mix in the tank is unnecessary. The use of a disaccharide, a binder and a surfactant together permits inclusion of a more concentrated amount of the plant growth regulator, at least 40%. This more concentrated formulation enhances utilization, as will be described in greater detail in the subsequent paragraphs.

The Compositions

The formulation is granular. As used herein, the term "granular" refers to a solid composed of particles visible to the unaided eye. A granule is an agglomerate of fine particles.

The phrase "plant growth regulator" as used herein connotes a product which serves to modify the normal sequential development of a treated plant to agricultural maturity without killing the plant. Such modification may result from the effect of the material on the physiological processes of the plant, or from the effect of said material on the morphology of the plant. These modifications may also result from any combination or sequence of physiological or morphological factors.

The plant growth regulator may be a gibberellin, an auxin, an organic acid, a cytokinin, an ethylene biosynthesis inhibitor, or a combination thereof. Suitable ethylene biosynthesis inhibitors include aminoethoxyvinylglycine; suitable auxins include indole-3-acetic acid and indole butyric acid; suitable organic acids include a-naphthyl acetic acid and suitable cytokinins include 6-benzyladenine or 6-benzylaminopurine (6-BA) and 6-furfurylamino purine (kinetin).

The term "gibberellins" encompasses diterpenoids having a tetracyclic ring system. In terms of their nomenclature, gibberellins were numbered in order of their discovery, so the numbering does not signify the position of one particular substituent. The compounds have nineteen or twenty carbons, and four or five ring systems. Some examples of gibberellins include $GA_3$, commonly referred to as gibberellic acid; and $GA_4$ and $GA_7$, which are immediate precursors of $GA_3$. There are approximately 90 gibberellins, and all are encompassed by the general term "gibberellin", "gibberellins" or "gibberellic acid"; a presently preferred plant growth regulator. In the formulations, either a single gibberellin or a combination of two or more gibberellins may be the active ingredient.

The binder aids binding, disintegration and solubilization of the formulation. Suitable binders include alkylated vinyl pyrrolidone copolymers such as AGRIMER AL-10 and AGRIMER AL-10LC; cross-linked polyvinylpyrrolidones such as AGRIMER AT and AGRIMER ATF; copolymers of vinyl acetate and vinylpyrrolidone such as AGRIMER VA-6 and AGRIMER VA-7; lignosulfonates and sodium or calcium salts thereof such as MARASPERSE, VANISPERSE, BORRESPERSE, NORLIG, POLYFON and KRAFTSPERSE; unsulfonated lignins such as INDULIN AT; clays such as HYDRITE RS, microcrystalline celluloses such as AVICEL PH and LATTICE NT; methyl cellulose ethers such as METHOCEL; ethyl cellulose polymers such as ETHOCEL; starch (natural or modified); gluten; silicates and sodium or calcium salts thereof; magnesium aluminum silicates such as VEEGUM F; natural or modified lecithins such as BEAKIN, CENTROMIX or YELKIN; sugar alcohols such as NEOSORB, SORBOGEM, MANOGEM and MALTISWEET and polyethylene glycols, among others. A presently preferred binder is polyvinylpyrrolidone such as AGRIMER 15, AGRIMER 30, AGRIMER 60, AGRIMER 90 and PLASDONE.

The disaccharide is used as a diluent and as a granulating aid in the formulation. Suitable disaccharides include sucrose, lactose and maltose, hydrolyzed starches such as maltodextrin and corn syrup solids, sugar alcohols such as sorbitol and mannitol and other sugars such as fructose and glucose among others. A presently preferred disaccharide is lactose monohydrate.

In the formulation, the surfactant is used as a wetting agent, as well as a dispersing and granulating aid. Suitable surfactants include non-ionic surfactants, anionic surfactants and amphoteric surfactants. Non-ionic surfactants include ethoxylated sorbitan esters such as EMSORB, TWEEN, and T-MAZE; sorbitan fatty acid esters such as SPAN and ALKAMUL; sucrose and glucose esters and derivatives thereof such as MAZON, RHEOZAN and GLUCOPON; ethoxylated alcohols such as TRYCOL, BRIJ, ARMIX and PLURAFAC; ethoxylated alkylphenols such as IGEPAL, MACOL and TERGITOL; ethoxylated fatty amines such as TRYMEEN and ETHOMEEN; ethoxylated fatty acids such as EMEREST, ALKAMUL and TRYDET; ethoxylated fatty esters and oils such as ALKAMUL and ATLAS G; fatty acids such as ATLAS G-1556; glycerol esters such as MAZOL GMO; glycol esters such as GLYCOL SEG; lanolin-based derivatives such as AMERCHOL CAB; methyl esters such as OLEOCAL ME; monoglycerides and derivatives such as ETHOSPERSE G-26; propoxylated and ethoxylated fatty acids such as ANTAROX AA-60; block copolymers of ethylene oxide and propylene oxide such as PLURONIC or SURFONIC; silicone-based surfactants such as SILWET, BREAKTHRU and mixtures of organosilicon surfactant with non-ionic or ionic surfactants; polysaccharides, copolymers of acrylamide and acrylic acid; and acetylenic diol derivatives such as SURFYNOL 104 or tristyrylphenols such as SOPROPHOR among others. A presently preferred surfactant family is the ethoxylated sorbitan esters. Non-ionic surfactants such as polyoxyethylene (20) monolaurate (TWEEN 20 or POLYSORBATE 20) are presently most preferred.

Suitable anionic surfactants include phosphate esters such as EMPHOS and RHODAFAC; sulfates and sulfonates of oils and fatty acids such as POLYSTEP; sulfates and sulfonates of ethoxylated alkylphenols such as TRITON X-301; sulfates of dodecyl and tridecylbenzenes such as CALMULSE; sulfonates of condensed naphthalenes such as VULTAMOL; sulfonates of naphthalene and alkyl naphthalene such as MOREWET and sulfuosuccinates and derivatives such as MONAWET, among others.

Suitable amphoteric surfactants include lecithin and lecithin derivatives; and imidazolines and imidazoline derivatives such as MIRANOL, among others.

The tradenames used above for binders and surfactants often are common to a class or series of binders or surfactants. Therefore, where a tradename is mentioned, any binder or surfactant in the family including that tradename will be suitable.

Other components of the formulation may include additional surface active agents, stickers, spreader stickers, nematicides, systemic acquired resistance inducers, inert carriers, preservatives, humectants, dyes, U.V. (ultra-violet) protectants, buffers, flow agents, antifoams or other components which facilitate product handling and application.

Examples of inert carriers include inorganic minerals such as kaolin, mica, gypsum, fertilizer, carbonates, sulfates, or phosphates; organic materials such as sugar, starches or cyclodextrins; or botanical materials such as wood products, cork, powdered corn cobs, rice hulls, peanut hulls and walnut shells. A presently preferred antifoam is polydimethylsiloxane and a presently preferred carrier is sodium aluminosilicate.

It is also contemplated that the materials of this invention may be used in combination with other essential biologicals or beneficial microorganisms or active ingredients, such as herbicides, anti-microbials, fungicides, insecticides, nematicides, biological pesticides such as microbial pesticides, biochemical pesticides (semiochemicals, hormones or natural plant regulators), plant produced pesticides (botanicals) or plant nutrients.

The compositions of this invention may also be formulated as active mixtures which may include finely divided dry diluents, extenders, fillers, conditioners, and excipients, including various clays, diatomaceous earth, talc and the like and mixtures thereof.

A presently preferred composition contains technical grade active ingredient gibberellin; a disaccharide; a homopolymer of polyvinylpyrrolidone and a surfactant. A preferred technical grade active ingredient gibberellin is $GA_3$, since it is the most widely used plant growth regulator for agriculture, although other gibberellins, including but not limited to $GA_4$, $GA_7$ and combinations thereof or mixtures thereof may be utilized. The weight range of gibberellins in the formula can be from 40% to 80%.

The amount of disaccharide that can be used will depend upon the percent of gibberellin in the formula and may range between 5% to 96%.

When polyvinylpyrrolidone is used in the formulation, it may have a molecular weight range of 6,000 to 1,500,000. A presently preferred polymer is polyvinylpyrrolidone (PVP) having a mean molecular weight of 57,500 (range= 40,000 to 80,000 such as PVP K-30, AGRIMER 30, or PLASDONE). The weight range of polyvinylpyrrolidone in the formula may range between 0.1% to 4% depending upon the concentration of gibberellins and other additives.

A presently preferred specific composition includes 43 to 46% of gibberellic acid; 47 to 57% of lactose monohydrate, 1.4–2% POLYSORBATE 20; 0.7 to 2% polyvinylpyrrolidone (AGRIMER 30).

The present water-soluble granules can be contrasted to water-dispersible granules in that water-soluble granules dissolve in water upon mixing to form aqueous solutions, and can have a higher concentration of active ingredient than water-dispersible granules, which only disperse in water upon mixing with agitation to form aqueous suspensions.

A particular advantage of the water-soluble granular formulations described above is that they disperse and dissolve readily in water, without the need for extended or excessive agitation.

The compositions are made by blending ingredients, extruding and drying the extrudate to obtain the desired water-soluble granular formulation. Methods of making water-dispersible granules for agricultural uses are disclosed in EP 0 665 714 B1; and U.S. Pat. Nos. 5,589,438; 4,865, 842; 5,464,623; 6,087,306 and 6,013,272 among others. However, the present method for obtaining water-soluble granules, has not been previously disclosed.

The Methods

Gibberellins are known plant growth regulators. For example, U.S. Pat. No. 4,242,120 discloses a non-spray combination of a gibberellin with a low molecular weight carbohydrate such as saccharose, glucose, fructose or maltose to stimulate fructification; and U.S. Pat. No. 5,163,993 discloses a combination of gibberellin and a surfactant for thinning grape clusters. However, the water-soluble granular formulations detailed above have not been previously disclosed.

The formulations described above may be used to regulate plant growth of fruit-producing plants, vegetable-producing plants, row crops, vegetable crops, grasses or trees. The benefits of the use of the formulation vary, according to the type of fruit treated. For example, in grapes, treatment with the formulation can lead to cluster elongation, thinning and larger grapes. In oranges, lemons, limes and tangerines, the formulation can lead to a delay the aging of the rind and reduce disorders such as rind staining, water spotting, sticky or tacky surface, puffy rind or rupture under pressure. In cherries, the formulation may advantageously be used to produce larger, brighter colored and/or firmer fruit.

The formulation is preferably diluted in water and sprayed on the plant or tree to be treated. The spraying may be by conventional ground or aerial application equipment. Spray volumes are variable depending upon the orchard or crop, growth stage and climatic conditions. The range may be 5 gallons to 300 gallons/acre or higher. A presently preferred range is between 250 to 300 gallons per acre by pressurized spray application equipment. To prepare a formulation for application, a tank is half-filled with water, followed by spray addition of adjuvant, and then addition of plant growth regulator, followed by addition of more water and then mixed for at least 15 minutes prior to actual spraying.

Alternatively, the formulation may be directly applied to the soil (in which the plant will be grown or is growing) with or without granular fertilizers for the improved growth and maintenance of crops.

Moreover, the formulation may be applied to seeds to achieve the same effect. The seed may be rice or paddy, alfalfa, cotton, sorghum, soybeans, corn or other vegetables, ornamental or turf and pasture grass seed, among others.

The concentration of the plant growth regulator will vary depending upon the type of fruit is to be treated, the peculiarities of the locale, and the desired result. In general, the composition may be applied at a field rate of from about 0.02 to about 50/lbs per acre; preferably at a rate of from about 0.1 to about 5/lbs per acre and most preferably at a rate of from about 0.5 to about 3 lbs/acre.

A single application may be enough, though depending upon the particular fruit and desired results, multiple applications may be made.

The granular formulations may be applied to plants, soil or seeds in conjunction with other adjuvants. An adjuvant is a material added to a tank-mix to aid or modify the action of an agrichemical, or the physical characteristics of the mixture. There are several types of tank-mix adjuvants such as buffering agents, compatibility agents, defoaming agents, modified vegetable oil concentrates, non-ionic surfactants, penetrants, phytoblend oil, spreader/sticker, sticker, vegetable oil concentrates, or other components such as acidifiers, humectants, activators and crop oil concentrates. An example of a buffering agent is BUFFER-X, a mixture of alkylarylpolyethoxyethanol, fatty acids, glycol ethers, D-alkyl benzene dicarboxylate and isopropanol; an example of a compatibility agent is LATRON AG-44M, a mixture of alkylarylpolyoxyethylene glycol and phosphate ester surfactants; an example of a defoamer is FOAM BUSTER, a dimethylpolysiloxane; examples of spreader-stickers are LATRON B-1956, a modified phthalic glycerol alkylated resin and SURFIX, a beta-pinene polymer and an example of a sticker is BOND, a synthetic latex polymer.

The type of adjuvant and application rate will vary depending upon the adjuvant used, crop, crop growth, climatic conditions, desired effect and which other tank mix additives, if any are utilized. Other tank mix additives may be pesticides or foliar nutrients for example.

The formulations described above are particularly advantageous because they are easier to handle for spray application. When the solid formulation is measured out for dilution in aqueous solution, it has an excellent attrition resistance property with minimum potential for dust generation during handling, is easier to measure and dissolves rapidly. Moreover, the water-soluble granular formulations contain a more concentrated amount of plant growth regulator than other types of solid formulations such as water-dispersible granules; thus the water-soluble granular formulations can be packed, shipped and stored more compactly.

As used herein the term "plant" includes fruit-producing plants, vegetable-producing plants, row crops, vegetable crops, grasses and trees.

The fruit may be grapes, cherries, lemons, limes, oranges, grapefruit, strawberries, pineapples, stone fruits, apples, pears, blueberries or tangerines. The row crop may be cotton, soybeans, corn, sugar cane or rice, among others. The vegetable crops may be lettuce, artichokes, celery or peppers among others. The grasses may be Bahaigrass (*Paspalum notatum* Flugge), Bentgrass (*Agrostis* L.), Bermudagrass (*Cynodon dactylon* L.), Carpetgrass (*Axonopus affinis* Chase), Kentucky bluegrass (*Poa pratensis* L.), Canada Blugrass (*Poa compressa* L.), Buffalograss (*Buchloe dactyloides* (Nutt.) Englem.), Fescue grasses (*Festuca*), annual Rye grass (*Lolium* L. *multiflorum* Lam.), perennial Rye grass (*Lolium perenne* L.), Saint augustinegrass (*Stenotaphrum secundatum* Kuntze), Japanese lawngrass (*Zoysia japinica* Steud.), Centipedegrass (*Eremochloa ophiuroides* (Munro) Hacck, other turf grasses for residential or commercial establishments, among others.

Of course, the present invention is not limited to the particular embodiments and modes of operation described herein and it is possible to imagine a number of variations in the details without departing from the scope of this invention.

The examples below are presented to describe preferred embodiments and utilities of the invention and are not meant to limit the invention unless otherwise stated in the claims appended hereto.

EXAMPLE 1

The water-soluble, granular formulation of plant growth regulator was prepared as follows.

First, the plant growth regulator, gibberellic acid, and the disaccharide, lactose monohydrate, were sized to optimize particle size in order to obtain a homogeneous mixture as well as to increase rate of solubility of the granules. The gibberellic acid solid particles were milled such that 88% of the particles pass through a 100 mesh sieve (150 micrometers), and the lactose monohydrate solid particles were selected such that a minimum of 98% of the particles pass through an 80 mesh (180 micrometers) sieve. The components thus processed were blended together until a homogeneous mixture was obtained.

Next, binder stock solution was prepared as follows. Polyvinylpyrrolidone (AGRIMER 30, available from International Specialty Products, Inc.) was slowly added to filtered deionized water which was pre-heated to 45° C. to 55° C., and then mixed until a clear solution is obtained. The mixture was then cooled. Next, a surfactant such as an ethoxylated sorbitan ester (TWEEN 20, available from Uniqema) was added to the aqueous binder solution with stirring to form an aqueous binder and surfactant mixture.

The aqueous binder and surfactant mixture was then added at a controlled rate to the blend of sized particles of plant growth regulator and disaccharide. The resulting non-sticky moist mass was extruded through an extruder and then dried to less than 3% moisture and screened to obtain the final water-soluble granular plant growth regulator formulation. The desired product was recovered after sieving granules passing through a 10 mesh sieve having openings of 2000 micrometers and retained on a 30 mesh sieve having openings of 600 micrometers.

The procedure described above was utilized to prepare the formulations 1–3 representative of the present invention described below in Tables 1–3. Representative samples of the formulation 2 were subjected for four weeks to an accelerated temperature of 54° C. and for three months at constant 40° C., 5° C., 25° C. and 30° C. Both physical and chemical properties (% $GA_3$) of the formulations remained stable during the test period.

The above method is a specific example of the preparation of a formulation. Generally, gibberellic acid of a particle size in the range of 30 micrometers to 250 micrometers and lactose monohydrate of a particle size in the range of 30 micrometers to 180 micrometers will be useful for preparing the present formulations.

TABLE 1

Formulation 1

| Component | type | source | weight % |
|---|---|---|---|
| Gibberellin $GA_3$ | plant growth regulator | Abbott Laboratories | 45.6 |
| lactose monohydrate | disaccharide | Foremost Farms, USA | 50.6 |
| polyvinylpyrrolidone | binder | AGRIMER 30, ISP Technologies, Inc. | 0.8 |
| block copolymers of ethylene oxide and propylene oxide | surfactant | PLURONIC L-62, BASF Corp. | 3.0 |

TABLE 2

Formulation 2

| Component | type | source | weight % |
|---|---|---|---|
| Gibberellin GA$_3$ | plant growth regulator | Abbott Laboratories | 45.6 |
| lactose monohydrate | disaccharide | Foremost Farms, USA | 51.9 |
| polyvinylpyrrolidone | binder | AGRIMER 30, ISP Technologies, Inc. | 1.0 |
| polyoxyethylene 20 monolaurate | surfactant | TWEEN 20, available from Uniqema | 1.5 |

TABLE 3

Formulation 3

| Component | type | source | weight % |
|---|---|---|---|
| Gibberellin GA$_3$ | plant growth regulator | Abbott Laboratories | 45.6 |
| lactose monohydrate | disaccharide | Foremost Farms, USA | 51.7 |
| lecithin | binder | ULTRALEC P, available from ADM | 1.2 |
| polyoxyethylene 20 monolaurate | surfactant | TWEEN 20, available from Uniqema | 1.5 |

EXAMPLE 2

To determine the effectiveness of the water-soluble granular formulation, a representative example of a water-soluble granular gibberellic acid formulation (Formulation 2, of Example 1) was evaluated in the field against a commercially available formulation of a soluble powder gibberellin formulation (PROGIBB 2X, available from Valent BioSciences Corp.) to determine the effects on Red Globe grape production.

The test formulations were prepared as follows. 200 grams of the commercially available PROGIBB 2x equivalent to 40 grams of active ingredient were dissolved in 500 gallons of water in a commercial-size spray tank. Similarly, 100 grams of the experimental water-soluble granular formulation of the present invention (Example 2) equivalent to the same 40 grams of active ingredient was dissolved in 500 gallons of water in a commercial-size spray tank. Both spray solutions also contained a commercial adjuvant, LATRON B-1956, a water-dispersible resin-based non-ionic surfactant (modified phthalic glycerol alkylated resin, available from Rohm & Haas), at 0.05% wt/wt.

The field experiment was conducted on a Red Globe grape orchard in the western United States. Each formulation diluted in water was sprayed at a single application rate of 20 grams of active ingredient in 250 gallons of water/acre on Red Globe grapes. The berries were 14–16 mm in diameter at the time of treatment. Three months after the treatment, the grapes were harvested and the data on the size of berries in grams and percent soluble solids (% Brix) were recorded.

Soluble solids are measured by a standardized refractometer technique. An increase in soluble solids indicates that the quality of the berries has improved; as it indicates sweeter berries.

The data presented in Table 4 show that the water-soluble granules of the present invention surprisingly and significantly increased both berry size and soluble solids compared to the standard formulation, even though the application rates on an active ingredient basis; variety and growth stage were similar for both treatments. Statistical analysis indicated that these numbers reflected actual improvements, and were not the result of random occurrences.

TABLE 4

Comparison of Effects of Gibberellin Formulation on Treatment of Red Globe Grapes

| Gibberellin Formulation | Berry Size (gms) | Mean % weight berry/weight soluble solids |
|---|---|---|
| water-soluble granule | 15.2 a | 9.2 a |
| water-soluble powder | 13.6 b | 8.0 b | mean separation determined by Duncan's multiple test, p = 0.05

EXAMPLE 3

To determine the effectiveness of a water-soluble granular formulation, a representative example of a water-soluble granular gibberellic acid formulation (Formulation 2 of Example 1) was evaluated in the field against a commercially available formulation of a soluble powder gibberellin formulation (PROGIBB 2X, available from Valent BioSciences Corp.) for effects on Thompson Seedless grape production.

The test formulations were prepared as follows. 640 grams of commercially available PROGIBB 2X equivalent to 128 grams of active ingredient was dissolved in 500 gallons of water in a commercial-size spray tank. Similarly, 320 grams of water-soluble granular formulation of the present invention (Formulation 2 of Example 1) equivalent to the same 128 grams of active ingredient was dissolved in 500 gallons of water in a commercial size spray tank. Each spray solution also contained a commercial adjuvant, LATRON B-1956, a water-dispersible, resin-based, non-ionic surfactant (modified phthalic glycerol alkylated resin, available from Rohm & Haas), at 0.05% wt/wt.

The field experiment was conducted in a Thompson Seedless grape orchard in the western United States. Each formulation diluted in water was applied two times, the first time when the berries were 4–6 mm in diameter, and a second time when the berries were 8–10 mm in diameter. Both times, application rates were kept equal for both formulations, at 64 grams of active ingredient sprayed at a rate of 250 gallons/acre. Three months after the second application, the grapes were harvested and the size of the berries in grams and % soluble solids (% Brix) were recorded. The data presented in Table 5 show that the water-soluble granules of the present invention surprisingly and significantly increased both berry size and soluble solids when compared to the standard formulation, even though the application rates on an active ingredient bases, variety and growth stage were similar for both treatments. Statistical analysis indicated that these numbers reflected actual improvements, and were not the result of random occurrences.

TABLE 5

Comparison for Treatment of Thompson Seedless Grapes

| Gibberellin Formulation | Berry Size (gms) | Mean % weight berry/weight soluble solids |
|---|---|---|
| water-soluble granule | 18.6 a | 7.3 a |
| water-soluble powder | 18.3 b | 6.9 b | mean separation determined by Duncan's multiple range test, p = 0.05

All references cited are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims:

We claim:

1. A water-soluble granular gibberellin composition comprising:
   at least 40 weight % based upon the total weight of the composition of at least one gibberellin;
   at least one binder;
   at least one member selected from the group consisting of disaccharides,
   sorbitol, mannitol, glucose and fructose; and
   at least one surfactant.

2. The composition of claim 1 wherein said binder is selected from the group consisting of polyvinylpyrrolidones, lignosulfonates, lignins, lecithins, starches, glutens, polyethylene glycols and combinations thereof.

3. The composition of claim 1 wherein said disaccharide is selected from the group consisting of sucrose, lactose, maltose, maltodextrin, corn syrup solids, and combinations thereof.

4. The composition of claim 1 wherein said surfactant is selected from the group consisting of ethoxylated fatty acids, glycol esters, ethoxylated alcohols, sorbitan fatty acid esters and combinations thereof.

5. The composition of claim 1 further comprising an additional component selected from the group consisting of surface active agents, stickers, spreader stickers, nematocides, systemic acquired resistance inducers, anti-foaming agents, preservatives, humectants, dyes, U.V. protectants, buffers, flow agents, carriers and combinations thereof.

6. The composition of claim 1 having from about 40 to about 80 weight percent plant growth regulator, from about 0.1 to about 10 weight percent binder, from about 5 to about 95 weight percent disaccharide and from about 0.1 to about 10 weight percent surfactant wherein all the percentages are based upon the total weight of the granular composition.

7. The composition of claim 1 wherein said disaccharide is lactose monohydrate, said binder is polyvinylpyrrolidone and said surfactant is polyoxyethylene 20 sorbitan monolaurate.

8. The composition of claim 1 further comprising at least one additional component selected from the group consisting of anti-foaming agents, preservatives, humectants, dyes, U.V. protectants, buffers, flow agents, carriers and combinations thereof.

9. The composition of claim 1 further comprising at least one additional plant growth regulator selected from the group consisting of auxins, cytokinins, organic acids, ethylene biosynthesis inhibitors and combinations thereof.

10. The composition of claim 7 having from about 40 to about 50 weight percent gibberellin, from about 0.1 to about 4 weight percent polyvinylpyrrolidone, from about 40 to about 60 weight percent lactose monohydrate and from about 0.5 to about 5 weight percent polyoxyethylene 20 monolaurate wherein all the percentages are based upon the total weight of the granular composition.

11. A water-soluble granular gibberellin composition comprising:
   from about 40 to about 50 weight percent of at least one gibberellin;
   from about 0.1 to about 4 weight percent polyvinylpyrrolidone;
   from about 40 to about 60 weight percent lactose monohydrate; and
   from about 0.5 to about 5 weight percent polyoxethylene 20 monolamate wherein all the percentages are based upon the total weight of the granular composition.

12. The composition of claim 11 further comprising at least one additional component selected from the group consisting of additional surface active agents, additional binders, anti-foaming agents, preservatives, homectants, dyes, U.V. protectants, buffers, flow agents, carriers and combinations thereof.

13. The composition of claim 11 further comprising at least one additional plant growth reglator selected from the group consisting of auxins, cytokinins, organic acids, ethylene biosynthesis inhibitors and combinations thereof.

* * * * *